(12) United States Patent
Struik et al.

(10) Patent No.: US 11,559,332 B2
(45) Date of Patent: Jan. 24, 2023

(54) SYSTEM FOR CONNECTING A CONNECTION DEVICE TO A BONE

(71) Applicant: ArthroSave Holding B.V., Culemborg (NL)

(72) Inventors: Thijmen Struik, Utrecht (NL); Floris Paulus Jacobus Gerardus Lafeber, Utrecht (NL); Karianne Hilde Lindenhovius, Utrecht (NL); Hubertus Paul Maria Ter Braak, Utrecht (NL)

(73) Assignee: ArthroSave Holding B.V., Culemborg (NL)

( * ) Notice: Subject to any disclaimer, the term of this patent is extended or adjusted under 35 U.S.C. 154(b) by 526 days.

(21) Appl. No.: 16/481,353

(22) PCT Filed: Jan. 29, 2018

(86) PCT No.: PCT/EP2018/052058
§ 371 (c)(1),
(2) Date: Jul. 26, 2019

(87) PCT Pub. No.: WO2018/138307
PCT Pub. Date: Aug. 2, 2018

(65) Prior Publication Data
US 2019/0388121 A1 Dec. 26, 2019

(30) Foreign Application Priority Data

Jan. 27, 2017 (WO) ................. PCT/EP2017/051851

(51) Int. Cl.
*A61B 17/64* (2006.01)
(52) U.S. Cl.
CPC ................. *A61B 17/6458* (2013.01)

(58) Field of Classification Search
CPC .................................................. A61B 17/6458
(Continued)

(56) References Cited

U.S. PATENT DOCUMENTS

| 4,127,119 A | * | 11/1978 | Kronner | ................. A61B 17/62 |
| | | | | 606/56 |
| 5,047,029 A | * | 9/1991 | Aebi | .................. A61B 17/7008 |
| | | | | 606/264 |

(Continued)

FOREIGN PATENT DOCUMENTS

WO     WO2017016611 A1    2/2017

OTHER PUBLICATIONS

International Preliminary Report on Patentability for International Application No. PCT/EP2018/052058 dated Jul. 30, 2019, 7 pages.

*Primary Examiner* — Eduardo C Robert
*Assistant Examiner* — David C Comstock
(74) *Attorney, Agent, or Firm* — Peter W. Schroen; Bret E. Field; Bozicevic, Field & Francis LLP

(57) ABSTRACT

System for connecting a connection device to a bone with a bone pin, wherein the system comprises a connection device provided with an opening for receiving the bone pin, and wherein the system further comprises a locking device arranged to be received in the opening of the connection device and which is arranged to engage the bone pin for locking the bone pin with respect to the connection device, wherein the locking device is movable between a locked position, wherein the bone pin is locked with respect to the connection device, and an unlocked position wherein the bone pin is movable with respect the connection device, wherein the system further comprises a blocking mechanism for at least partially blocking the opening in the connection device upon removal of the bone pin from the opening.

21 Claims, 8 Drawing Sheets

Figure 1A:
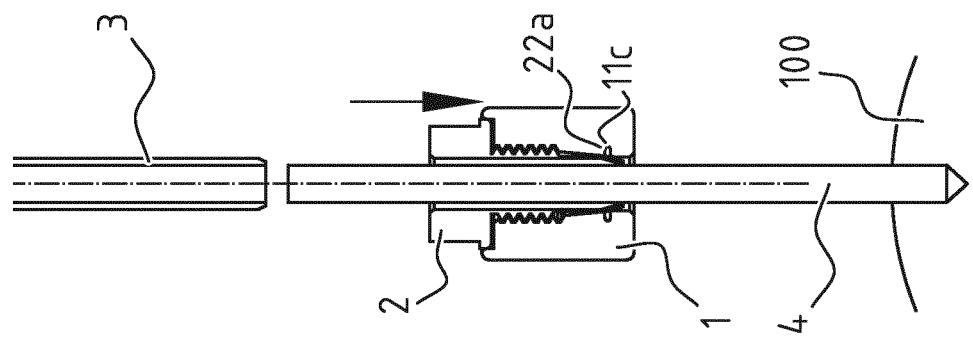

(58) Field of Classification Search
USPC ...... 606/59; 403/9, 204, 289, 290, 306, 314, 403/338, 357, 359.5, 367, 368, 371, 372, 403/373, 374.1, 376
See application file for complete search history.

(56) References Cited

U.S. PATENT DOCUMENTS

| | | | |
|---|---|---|---|
| 7,118,303 B2* | 10/2006 | Doubler | F16B 39/023 411/75 |
| 8,029,505 B2* | 10/2011 | Hearn | A61B 17/66 606/56 |
| 2006/0155275 A1* | 7/2006 | Dongar | A61B 17/60 606/59 |
| 2012/0253410 A1 | 10/2012 | Taylor et al. | |

* cited by examiner

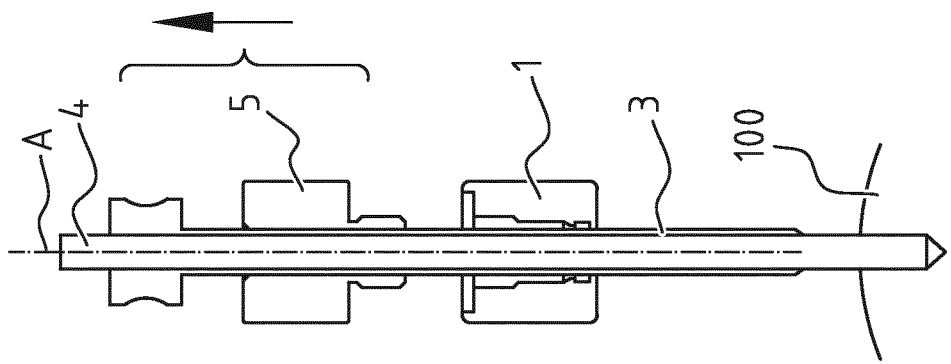
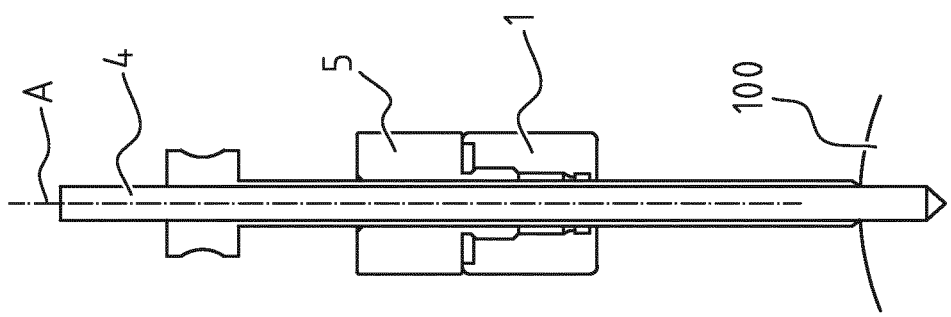
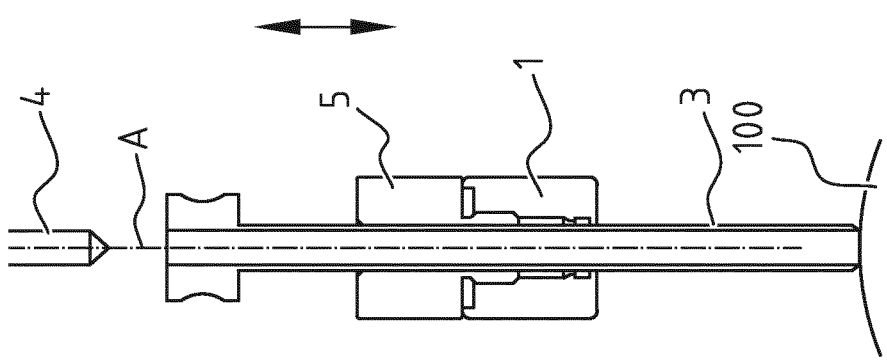
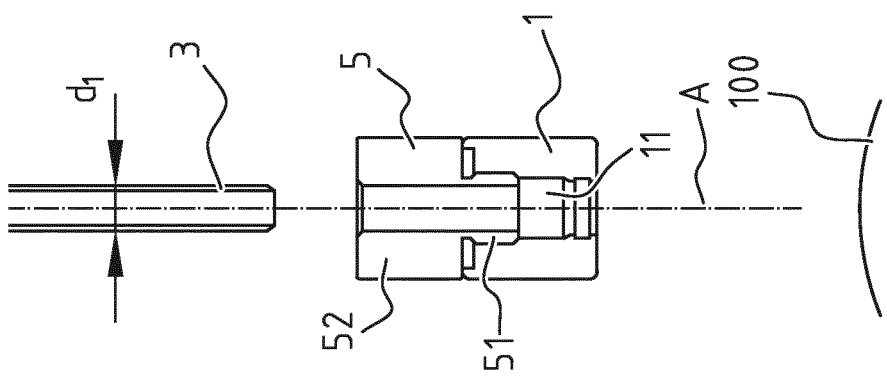

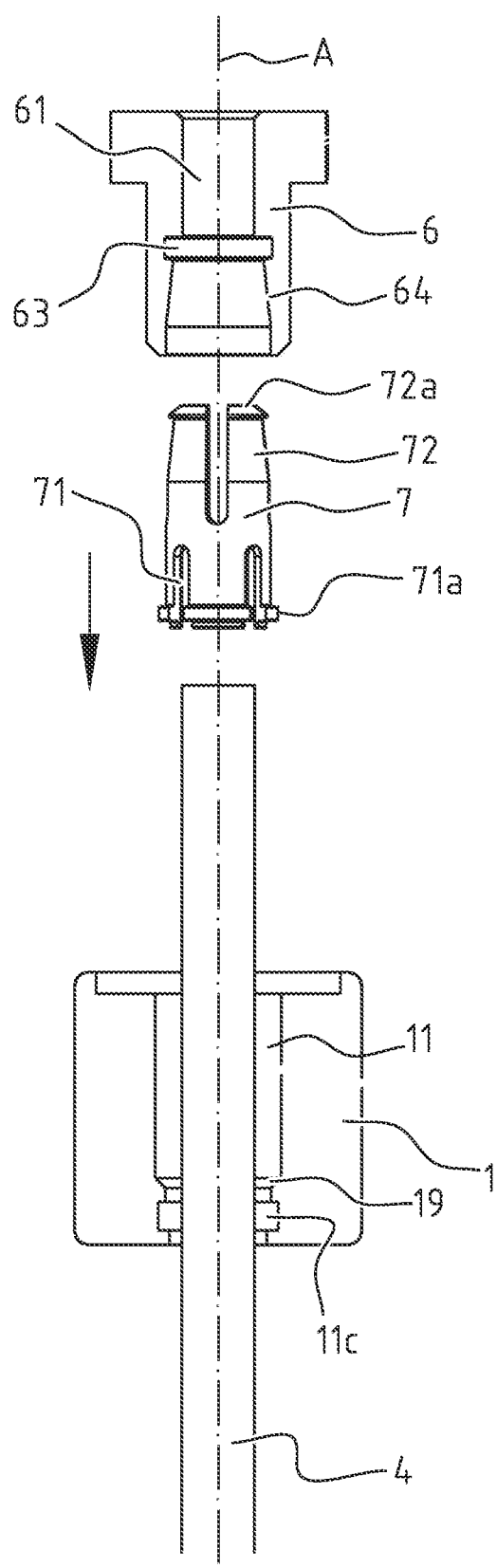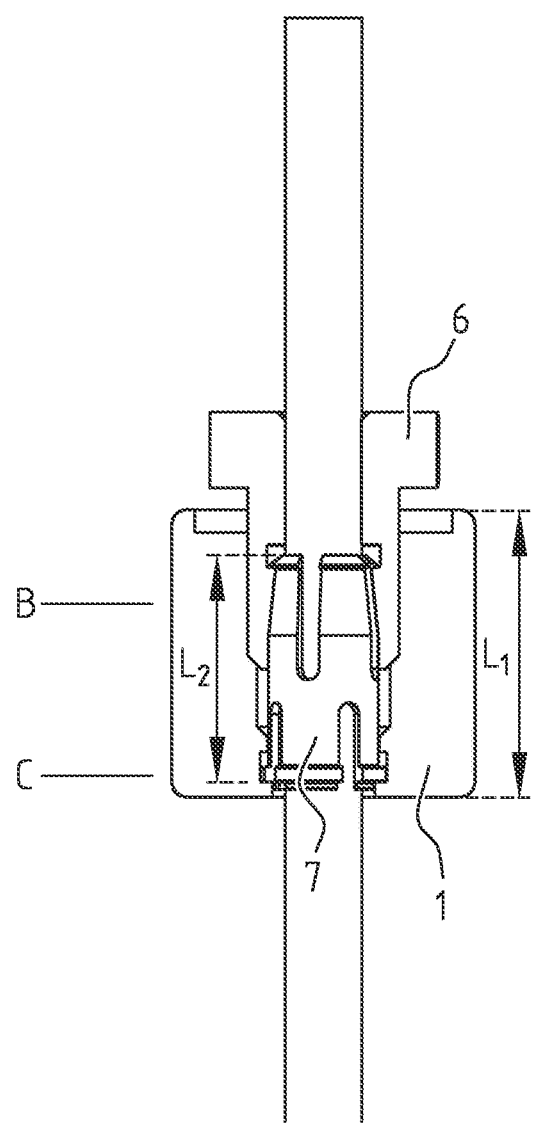
FIG. 3A
FIG. 3B

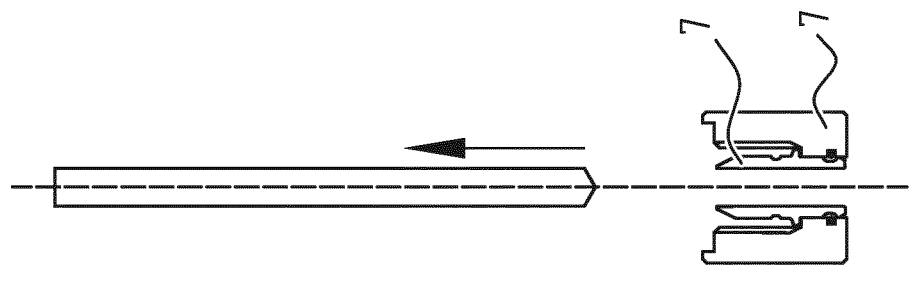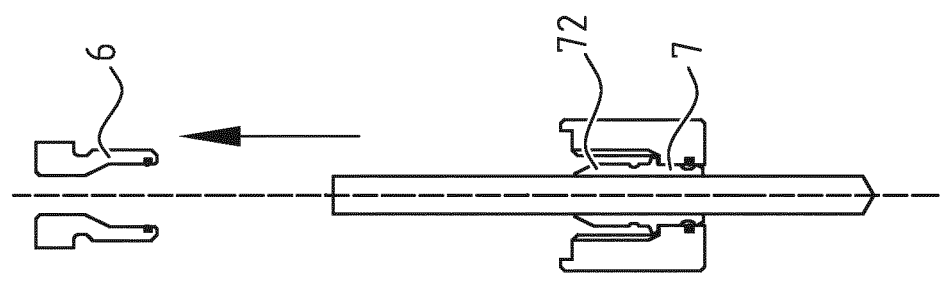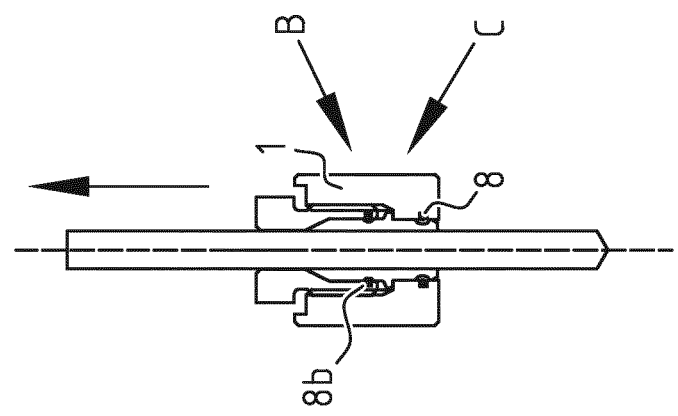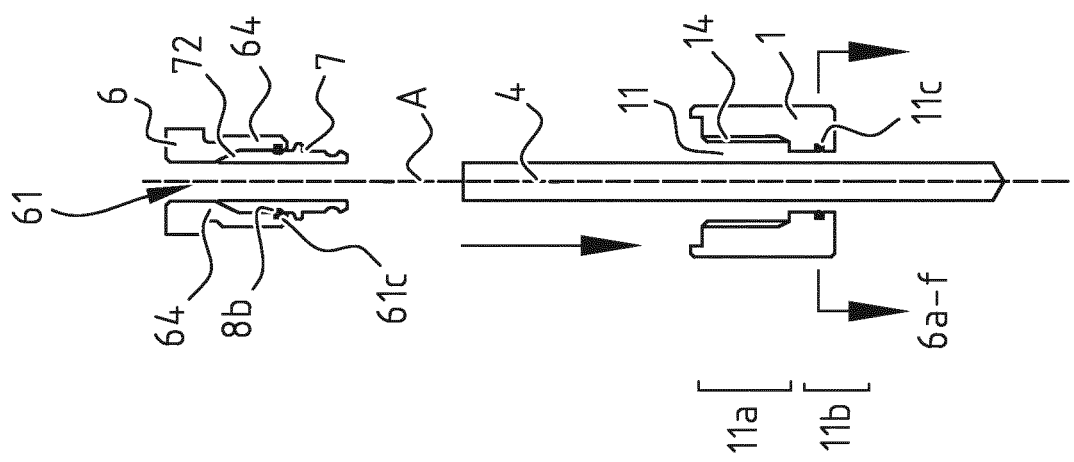

SYSTEM FOR CONNECTING A CONNECTION DEVICE TO A BONE

The present invention relates to a system for connecting a connection device to a bone.

The always growing need for healthcare is accompanied by an increasing need for resources. In order to maintain and improve the level of care, a more effective and efficient use of resources, including costs of care, is demanded. In this light, the reusability of medical devices needs consideration. Besides these aspects, the reusability of medical devices is of influence on the safety of devices and to safety issues concerning the application of those devices, known as quality control.

Different categories of medical devices require different approaches in quality control with respect to their use. A common measure for reducing the risk of failure and therewith posing risk to a patient, is found in the development of single-use or disposable medical devices. This measure is often seen as an obvious choice when high risk products are considered (e.g. needles, scalpel blades and syringes). In addition, the regulations for disposable devices are less demanding for developers of medical devices, since quality during use can be more easily ensured. In case of a clear need for a single-use product, it might be stated that a developer has to incorporate a technical solution for making a device a disposable device. Or the other way, the developer has to state that multiple use is not part of the intended use and will lead to off-label use without guarantee of quality after its first use.

On the other hand, the choice for a reusable system may have a beneficial influence on costs within healthcare as in general, reuse of devices can be less costly per procedure than using disposable devices, especially when measures are taken for extending the lifetime of a product. In the field of medical devices, mostly initiated by end-users and developers, the options for reuse of devices labeled as single-use devices is explored. A reduction in e.g. costs of a procedure may for specific categories of devices be reduced without introducing additional risks for a patient.

For many medical devices or attributes however, the need for single-use does not easily become clear from its intended use, particularly for the end-user. Devices that are generally accepted to pose a low risk in case of reuse or failure, are easily overlooked. In these cases such devices may be reused without quality control, which results in use beyond the intended use. The lack of functional limitations of a medical device after use, allows for reuse of a device by the end user. Limiting measures, including the implementation of (partial) disposable components and visual markings may improve the quality of care by introducing proper conditions for quality control of medical devices that can be reused but need quality control to prevent off-lable use.

It is a goal of the present invention, next to other goals, to provide a cost effective, easy to use, reliable and/or safe system for connecting a connection device to a bone with a bone pin wherein at least one of the above mentioned problems is at least partially solved.

This goal, amongst other goals, is met by a method according to the present disclosure.

According to the invention a system for connecting a connection device to a bone with a bone pin is provided, wherein the system comprises a connection device provided with an opening for receiving the bone pin, and wherein the system further comprises a locking device arranged to be received in the opening of the connection device and which is arranged to engage the bone pin for locking the bone pin with respect to the connection device, wherein the locking device is movable between a locked position, wherein the bone pin is locked with respect to the connection device, and a unlocked position wherein the bone pin is movable with respect the connection device.

Such a device is for instance known from the copending international patent application with application number PCT/EP2015/067547, the contents of which are hereby incorporated by reference. In the above described system, a bone pin, or similar fixation element such as a bone wire, can be connected to a connection device, typically in the form of a connection block, provided with an opening extending between an upper and a lower surface of said connection device. When the connection device, which may be part of an orthopaedic device, is correctly placed with respect to the patient and the bone pin, a locking device may be used to interlock the pin to the connection device. The locking device is hereto movable from an unlocked position, in which the bone pin is movable, in particular slidable, with respect to the connection device, and a locked position, wherein the bone pin is locked with respect to the connection device.

Preferably, the locking device has an inner diameter substantially corresponding to the diameter of the bone pin. According to a preferred embodiment, the locking device has an annular body having an outer diameter corresponding to the diameter of the opening of the connection device and an inner diameter suitable for engaging and locking the bone pin. The outer surface having the outer diameter is then arranged to efficiently connect to the connection device due to the matching diameters. A suitable interconnection between the locking device and the connection device is obtained if the connecting device and the locking device are providing with cooperating interconnecting means, for instance in the form of threading. As an alternative, or in addition thereto, it may however also be possible that the locking device and the connection device interconnect at another location than the outer surface of the locking device.

The inner surface of the locking device is then preferably arranged to be able to lock the bone pin by engagement in the locked position. This prevents movement between the locking device and the bone pin, such that also relative moment of the bone pin with respect to the connection device is prevented.

It is preferred that the locking device is movable from the locked position to the unlocked position. This allows a practitioner to adjust the relative position of the connection device and the bone pin or for removal of the connection device from the bone pin. To however prevent reuse of the connection device, in particular upon removal of the bone pin from the locking device, the system according to the invention comprises a blocking mechanism for at least partially blocking the opening in the connection device, preferably after removal of a bone pin from the opening of the connection device. This prevents, or at least makes it more difficult, to reuse the connection device with for instance another, or the same, patient. The blocking mechanism preferably blocks the opening such that the opening is made unsuitable for insertion of a component of the system, such as the locking element or a bone pin. The blocking mechanism may block the opening as formed in the connection device directly, or the blocking mechanism may block any opening, for instance an opening in the locking device for receiving therein the bone pin. Also here, reuse of the system is prevented as the opening in the connection device is blocked by blocking the opening in the locking device.

According to a preferred embodiment, the blocking mechanism comprises a movable member which is movable to a position within the opening for blocking said opening. Upon removal of the bone pin or any other suitable element from the system, a movable member, which was preferably held in an unblocked position keeping the opening free, moves into the opening, thereby blocking the opening such that reinsertion of a component, preferably a bone pin, is restricted. The movable member may for instance be biased into the blocked position and held by a component in the unblocked position. Upon removal of said component, the movable member moves towards the blocked position. The movable member may for instance comprise a member provided in the wall of the opening which is movable from a position at least flush with said wall (i.e. substantially not protruding from said wall) to a position extending or protruding from said wall for blocking the opening.

According to a further preferred embodiment according to the invention, the system, or the blocking mechanism comprises, a retaining mechanism arranged for preventing removal of said locking device from said opening, preferably when the locking device is moved from the locked to the unlocked position. The retaining mechanism thus prevents removal of the locking device from the opening of the connection device, thereby blocking the opening and making the system unsuitable for reuse. The locking device is preferably retained in the opening such that removal by hand is not possible. A suitable tool may thus be used. Preferably, as will be discussed in greater detail below, at least a part of the locking device is retained in the opening such that said part is completely received in said opening. This makes removal of the locking device, or the part thereof, by hand difficult, if not impossible.

A reliable connection between the locking device and the connection device, in particular the opening thereof, is obtained if the movable member is arranged to interlock the locking device and the connection device. The movable member for instance forms a bayonet lock between the locking device and the connection device. It is preferred if at least one of the locking device and the connection device is provided with a recess for receiving said movable member for retaining the locking device in the opening. In the blocked position, the movable member is received in the recess, thereby preventing or obstructing removal of the locking device.

According to a further preferred embodiment, the retaining mechanism is arranged to allow insertion of the locking device into the opening and to prevent subsequent removal of the locking device from said opening. Hereto, the movable member may be biased towards the blocking position. Upon initial insertion of the locking device in the opening, the movable member is preferably urged towards the unblocked position, for instance using suitable guiding surfaces, to allow initial introduction of the locking device in the opening. The movable member is then, preferably after further insertion into the opening, received in the recess, from which the movable member cannot be removed without substantial or specified force. It is then preferred if the opening of the connection device, the movable member and/or the locking device is provided with a tapering surface for urging the movable member towards an unblocked position upon initial insertion of the locking device into the opening for guiding the movable member into the recess.

The movable member may be formed as an integral part of the opening or the locking device. The movable member may for instance be formed from the same material as and integrally with the connection device or the locking device. As an alternative, the movable member may be formed from another material, but integrally or connected with the connection device or the locking device. One of the locking device or the opening of the connection device may be provided with the movable member, wherein the other of the locking device or the opening of the connection device may be provided with the recess for receiving the movable member therein.

It is however preferred if, according to a further preferred embodiment, the movable member is formed as a separate part. This allows a better locking action as the material can be specifically chosen for this purpose. The movable member is preferably formed as a ring shaped member received in a groove formed in one of the opening or the locking device, wherein the ring shaped member is movable between a blocking position wherein the ring shaped member protrudes from said groove and an unblocked position wherein the ring shaped member does not protrude from said groove. In other words, in unblocked position, the ring shaped or annular shaped member is at least flush (at least does not substantially protrude) from the surface wherein the groove is formed. This surface may be the inner surface of the opening or the outer surface of the locking device. In this unblocked position, the locking device can be inserted into the opening.

In order to allow an efficient movement of the ring shaped member form the blocked to the unblocked position, for instance when initially inserting the locking device in the opening, according to further preferred embodiment, in the blocked position at least a part of the ring shaped member lies at a distance from the bottom of the groove. This part is thus movable towards the bottom, thereby allowing the part protruding from the open end of the groove to be received in the groove. Efficient locking is obtained when the part of member protruding from said groove lies at a distance from the bottom of the groove. This protruding part is then efficiently moved inwardly upon moving to the unblocking position.

To increase the blocking of the ring shaped member, the ring shaped member comprises two diametrically opposed parts protruding from the groove, or a plurality of preferably equidistant protruding parts. These engaging parts preferably have a substantially rectilinear shape at the inner diameter. This forms substantially rectilinear parts for engaging the locking device. Preferably, at the location of these engaging parts, the ring shaped member lies at a distance from the bottom of the groove as mentioned above. One surface, in particular the outer surface, lies at a distance of the bottom of the groove for providing movement space, while the opposite surface, for instance at the inner diameter, protrudes from the groove for forming the engaging parts.

The ring shaped member need not to be a closed, i.e. to form a full circular ring. It is possible that the ring shaped member has the form of a broken annulus, i.e. only a sector of a ring. The opening in the ring can then provide flexibility to the ring shaped member. Next to a circular shape, the ring shaped member may further have the shape of an ellipse, as seen in a plane perpendicular to the longitudinal axis of the opening. The vertices on the mayor axis may engage the bottom of the groove, while the vertices on the minor axis may form the engaging parts.

To ensure proper alignment in the groove for correctly receiving the locking element in the opening, it is preferred if the surface adjacent the bottom of the groove comprises, preferably at least in the blocked position, at least three contact points at mutual distances, preferably substantially equal mutual distances, on a circle having a diameter corresponding to the diameter of the bottom surface of said groove. The contact points are chosen on the perimeter of a circumscribed circle such that the centre of the ring shaped member remains substantially at the same location, i.e. remain aligned in the opening, upon moving between the blocked and unblocked positions. More preferably, the ring shaped member is arranged such that during insertion of locking device in the connection device, the tapering surface of the locking device has two contact points with the movable member. More preferably, said contact points are arranged such that the distance between each of said protruding parts and the longitudinal central axis of the opening remains substantially equal.

The ring shaped member preferably has the shape of at least two-thirds of a full annulus. This provides flexibility, while a good alignment is obtained. The deformation of the ring shaped member may however also, or as alternative, originate from the elastic properties of the material used.

The dimensions of the ring shaped member, in terms of inner and outer diameter, preferably corresponds to the dimensions of the groove wherein the member is seated. The groove for instance has a diameter at the location of bottom and a diameter at the location of the open end of the groove. The inner and outer diameter of the ring shaped member is formed accordingly.

The movable member in the form of a ring shaped member may have a circular cross-section. The diameter, or generally the size, of the cross-section of the ring shaped member may be adapted to adjust spring constant of the ring shaped member. A larger diameter will for instance result in a higher retaining force.

According to a further preferred embodiment, the movable member has an asymmetrical cross-section, seen along the plane perpendicular to the longitudinal axis of the opening. This allows for retaining the locking device more efficiently. The movable member, for instance in the form of the ring shaped member as mentioned above, may be formed as a barb. The movable member then preferably has a barb shaped cross-section for retaining the locking device upon removal thereof.

The movable member may then facilitate passing of the locking device in a first direction, to which end the cross-section may be provided with a tapering guiding surface at a first side as mentioned above, whereas passing in the other direction is prevented, for instance by a retaining surface at the other side, both seen in cross-sectional view. Preferably, a lower surface of the cross-section, seen in an insertion direction of the locking device from the upper surface of the connection device towards the lower surface thereof, is substantially flat for forming said retaining surface. Upon removing the locking device, said device will abut the retaining surface, thereby preventing removal thereof. The cross-section may for instance be generally triangular, wherein a base of said triangle is facing towards the lower surface of the connection device.

It is further preferred if the groove with the ring shaped member is formed in the opening of the connection device, wherein the protruding parts of the ring shaped member are received in a correspondingly shaped groove in the locking device. The ring shaped member is then movable between a blocking position, wherein the inner diameter of the ring shaped member is smaller than the inner diameter of the opening of the connection device, and an unblocked position wherein the inner diameter of the ring shaped member is substantially equal to or smaller than the inner diameter of the opening.

As mentioned above, it is preferred if the connection device and the locking device can be interconnecting using threading as an example of interconnecting means. The retaining mechanism is preferably arranged to operate separately from the interconnecting means. In other words, although the interconnecting means, for instance in the form of threading, itself may retain the locking device into the opening in at least the locked position thereof, moving the locking device to the unlocked position, for instance rotating the locking device in said opening, will not prevent removal of the locking device from the opening. The retaining mechanism is thus arranged to operate separately from the interconnection means. The interconnecting means can thus be used to connect the locking device to the connection device, and can preferably be used to clamp the bone pin due to the moving engagement surfaces as mentioned above, while the retaining mechanism retains the locking device in the opening, in both the locked and the unlocked position of the locking device. More preferably, even if the interconnecting means are disengaged, the retaining mechanism retains the locking device in the opening. As an alternative, the retaining means may be arranged to maintain the interconnecting means in the engaged position.

In order to achieve an efficient locking of the bone pin, the locking device according to a preferred embodiment comprises an engaging surface for engaging the bone pin, wherein the engaging surface is movable towards and from said bone pin between the unlocked position, wherein the bone pin is movable with respect to the engaging surface, and the locked position, wherein the engaging surface engages the bone pin for locking said bone pin with respect to the connection device by clamping. The engagement surface is preferably moveable radially inwardly towards the longitudinal axis of the bone pin.

The engaging surface may for instance be formed on movable or deformable parts of the locking device, such as tongues, which are movable towards and preferably also from the bone pin for locking the bone pin.

In order to be able to efficiently move the engaging surface to the locked position, the opening of the connection device preferably has a tapering diameter, seen along the longitudinal axis of the opening, for moving the engaging surface between the positions, upon longitudinal movement of the locking device with respect to the connection device. The tapering diameter, or at least varying diameter, of the opening then serves as a guiding surface for guiding the engagement surface towards the bone pin for engagement. To further improve the movement of the engaging surface, the locking device preferably comprises a correspondingly shaped tapering outer diameter.

As an alternative, it is also possible that only the locking device has a varying outer diameter, for instance a wedge shape, which urges the engaging surface onto the bone pin upon movement of the locking device into the opening.

The locking device may be formed as a single unit. This reduces the number of parts. It is however preferred that the locking device comprises an engaging element provided with at least one engaging surface and a separate driving element arranged to move the engaging element along the longitudinal axis of the opening for moving the engaging surface from the unlocked to the locked position. Preferably, the driving element and the connection device are provided with cooperating connecting means. Although threading can be used here, it is preferred if a retaining mechanism similar as the mechanism discussed above is used.

When the engagement element is arranged to be moved to the locked position upon movement in the opening along the longitudinal axis as explained above, it is preferred that the engaging element comprises at least one second engaging surface at a distance from the first engaging surface, seen along the longitudinal axis of the opening. This allows clamping at two locations of the bone pin, thereby improving the locking action. The driving element is then preferably provided with an opening for receiving the engaging element and wherein the opening of the driving element has a tapering diameter, seen along the longitudinal axis of the opening, for moving the second engaging surface between the unlocked and locked position upon longitudinal movement of the driving element with respect to the engaging element. Also the engaging element and the driving element are then provided with cooperating guiding surfaces for urging the engaging surface towards the bone pin. As said, this improves the locking action.

It is also possible that the driving element and the engaging element are only provided with the second engaging surface as mentioned above such that the engaging surface of the engaging member is moved towards the bone pin upon moving the driving element longitudinally with respect to the engaging element as explained. The opening of the connection device then not needs to be tapered. Movement of the engaging surface of the engaging element is then induces by relative movement between the driving element and the engaging element. The engaging element and the driving element may thereto be provided with cooperating guiding surfaces, for instance surfaces tapering along the longitudinal direction.

According to a further preferred embodiment wherein the retaining mechanism is arranged to retain the engaging element of the locking device in the opening after removal of the driving element. The engaging element then blocks the opening as explained above. Preferably, the engaging element is completely retaining the opening. The length of the engaging element is thus preferably smaller than the length of the opening. This makes it difficult, if not impossible, to remove the engaging element from the opening without proper tools.

This is in particular advantageous when the movement of the engaging surface of the engaging element is induced by relative movement between the driving element and the engaging element. Removal of the driving element will then result in unlocking of the bone by disengagement of the engaging surface. Upon removal or loosening of the driving element (which may thereto be provided with threading cooperating with threading in the opening), the pin can be removed. The engaging element however remains in the opening.

A system according to a further preferred embodiment further comprises a second retaining mechanism for retaining the engaging element and the driving element, wherein the retention force of the retaining mechanism between the engaging element is larger than the retention force of the retaining mechanism between the engaging element and the driving element. Upon removal of the driving element, the driving element will come loose from the engaging element, instead of the engaging element coming loose from the connection device. The engaging device will thus be retained.

An efficient system is then obtained if both retaining mechanisms are provided with a ring shaped member as mentioned above, wherein the spring constants of said ring shaped members are different. As mentioned above, this can be obtained if the diameter of the ring shaped element of the second retaining mechanism is larger than the diameter of the retaining mechanism between the engaging element and the driving element.

According to a further preferred embodiment, the locking device in the form of the engaging element and the driving element are supplied in a connected configuration. The driving element and the engaging element can then be advanced over the pin together. Tightening of the driving element (for instance by relatively moving the engaging element and the driving element) will then result in locking of the bone pin. Upon removal, the engaging element remains in the connection device due to the weaker interconnection between the driving element and the engaging element than the interconnection between the engaging element and the connection device.

A further preferred embodiment of the invention further comprises a guiding tube arranged to guide the bone pin from the connection device to the bone for connecting the bone pin to the bone, wherein the inner diameter of the guiding tube corresponds to the outer diameter of the bone pin and wherein the guiding tube can be slidably received in the opening, the guiding tube being slidable with respect to the connection device along an axis parallel to a longitudinal axis of the opening. Inserting the bone pins by drilling needs protection of the soft tissues during drilling by a guiding tube, sometimes also referred to as a cannula or sleeve, around the bone pin protecting soft tissue to be harmed by the rotating bone pin during drilling. To enable drilling of a bone pin through the connection device using the guiding tube and subsequent fixation of the bone pin after removal of the guiding tube to the connection device, a locking device is provided. In a preferred embodiment, rotation of the guiding tube is blocked during drilling.

The opening is arranged to slidably receive a guiding tube. This allows adjusting the relative position of the guiding tube to be adjusted with respect to the connection device. It is in particular preferred that the depth of the guiding tube in the patient can be adjusted, such that the guiding tube is adjusted such that the distal end of the guiding tube abuts the bone. This prevents damage to the tissue surrounding the bone upon drilling of the bone pin. Preferably, the guiding tube is only movable along the longitudinal axis of the opening.

According to a further preferred embodiment, the outer diameter of the guiding tube is larger than the inner diameter of the locking device or the locking element thereof. This means that if the locking device is retained in the opening, a guiding tube cannot be received in the opening of the connection device. The opening is thus blocked and this prevents reuse of the guiding tube and therewith of the system.

It is hereby preferred if the guiding tube is movable with respect to the connection device and bone pin such that the guiding tube is removable from the combination of the bone pin and the connection device and wherein the locking device is arranged to lock the bone pin after removal of the guiding tube. The locking device is only inserted after insertion of the pin into the bone and after removal of the guiding tube. The connection device can thus efficiently be moved over the pin.

Upon inserting the locking device in the opening, i.e. sliding the locking device over the pin, the retaining mechanism, for instance the movable member thereof, is moved from the blocked position to the unblocked position to allow the initial insertion of the locking device, to subsequently lock the locking device to the connecting device to prevent removal of said locking device from said opening, for instance when the locking device is later moved from the locked to the unlocked position. As mentioned above, the system may thereto comprise a suitable tapering surface for urging the movable member backwardly allowing the locking device to pass, to subsequently lock the locking device into the opening upon receipt of the movable member in the recess.

As said, the locking device preferably has an inner diameter substantially corresponding to the diameter of the bone pin. In this embodiment, the locking device can only be placed in the opening after the removal of the guiding tube, as the guiding tube would not fit in the locking device. Providing a locking device having an inner diameter corresponding to the outer diameter of the bone pin allows a good locking action, as for instance the engagement surface only needs to be displaced over a little distance to obtain a good clamping action.

As an alternative, the locking device has an inner diameter substantially corresponding to the outer diameter of the guiding tube in the unlocked position. This allows the locking device to be already in place in the opening when the guiding tube is guided in the opening. The locking device may then have a guiding function for guiding the guiding tube. When the guiding tube is removed after insertion of the pin in the bone, the engagement surface is moved towards the bone pin, thereby bridging the wall thickness of the then removed guiding tube, to clamp the bone pin.

According to a further preferred embodiment, the connecting device and/or the locking device (the driving element and/or the locking element) is made from a metal or a plastic. Suitable materials include aluminium, stainless steel, composites and polymers.

Figure 5B:
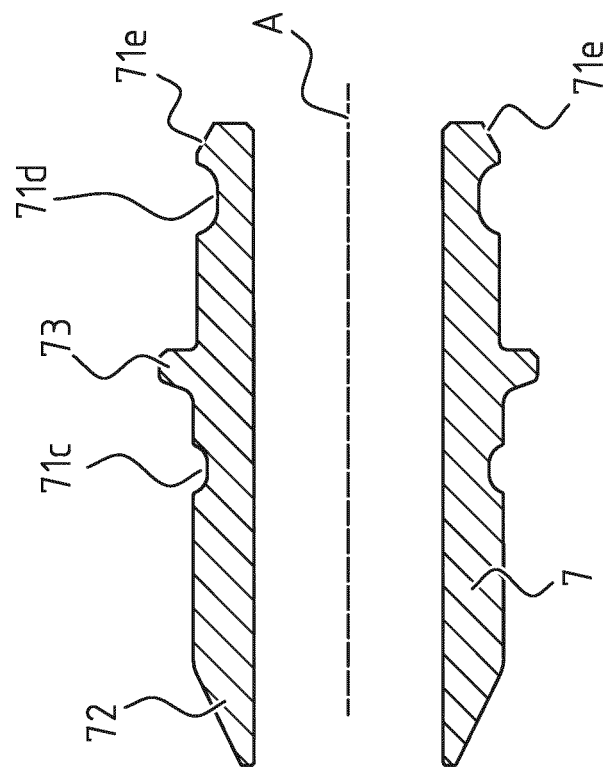
Figure 5A:
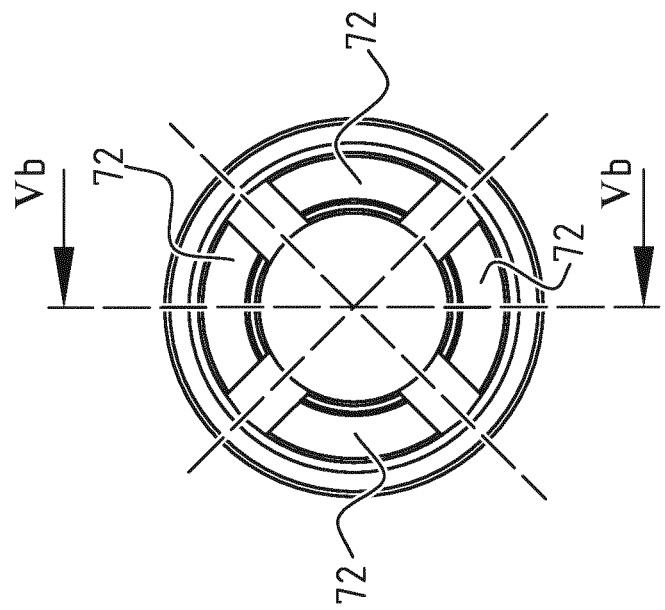
Figure 7:
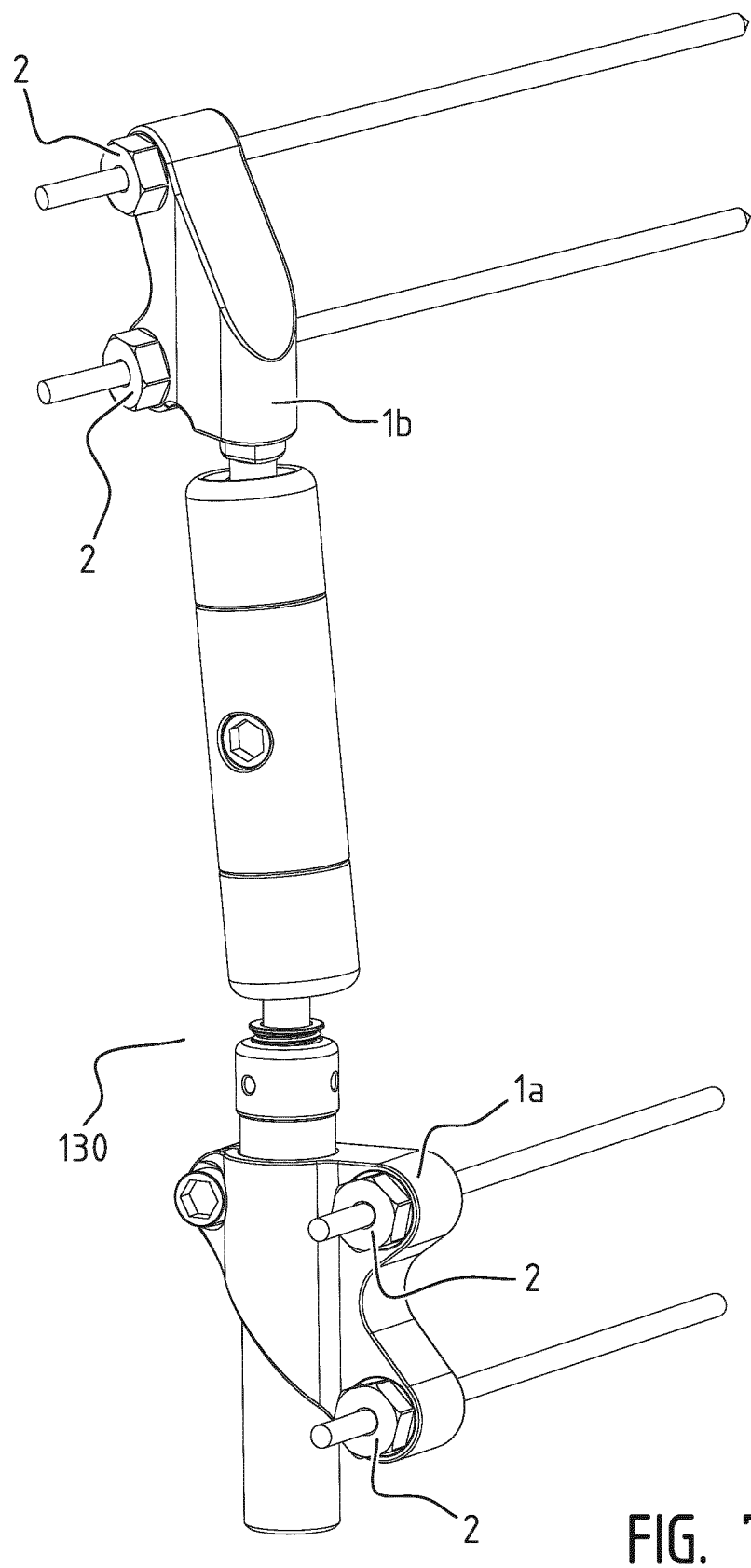
Figure 8:
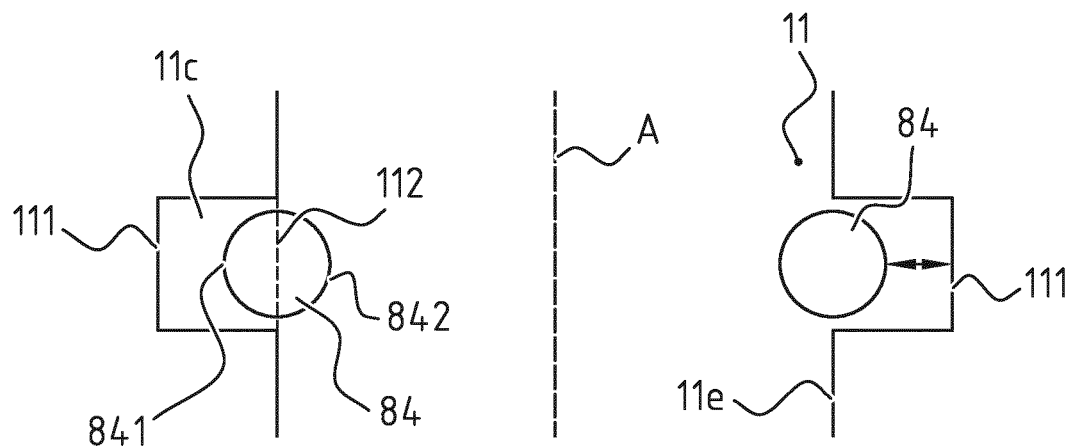

The present invention is further illustrated by the following Detailed Description and Figures, which show a preferred embodiment of the device and method according to the invention, and are not intended to limit the scope of the invention in any way, wherein:

FIGS. 1a-d schematically show a system and method for connecting a connection device to a bone;

FIGS. 2a-d schematically show a variant of the system of FIG. 1;

FIGS. 3a and b schematically show a variant of fixing a bone pin to a connection device;

FIGS. 4a-d schematically shows a further variant of fixing a bone pin to a connection device;

FIGS. 5a and b schematically show an engagement element of the locking device in front view and cross section;

FIGS. 6a-f show alternatives of spring members, both in blocking and unblocking positions;

FIG. 7 schematically shows an orthopaedic device using the system according to the invention;

FIG. 8 shows a cross-section of the groove in an opening of the connection device with a ring shaped spring; and FIGS. 9a-f show different cross-sectional shapes of the ring shaped spring.

The proposed system and method for application thereof relates to the assembly of a medical device, in particular a medical device for connecting a system to one or more bony structures, such that external loads applied to those bony structures are at least partially transferred via that system. Such systems include devices for medical procedures in traumatology and orthopedics such as bone lengthening, deformity correction, stabilization of complex fractures, joint fusion and joint distraction by means of external fixation. Such a system may for instance be used to connect an external fixator to the bones of the upper and the lower leg, known as the femur and tibia.

External fixation procedures are characterized by the fixation elements that connect the bony structures to the system of choice. The majority of the applied fixation elements consists of either metal wires that penetrate a bone and provide structural stiffness after tensioning, also known as Kirschner-wires, or consist of pins that can be screwed into the bone, sometimes requiring pre-drilling and tapping of the bony structure for optimizing the fixation capacity, also known as bone pins. An advantage of bone pins over wires is that the pins can be embodied as half pins, which only require an insertion site, although trans-fixating pins that fully penetrate a bony structure are also common. In general, multiple fixation elements for each bony structure are required for establishing a proper fixation between the bony structures and the system. In the following, the fixation elements, for instance in the form of wires and bone (half) pins as mentioned above, will also be referred to simply as bone pins.

In order to penetrate the bony structures, soft tissues such as skin and muscles that surround those structures need to be penetrated first. The insertion site of a wire or pin therefore needs to be considered carefully in determining a suitable location, such that risks of undesirable damage during fixation are minimized. Damage to other structures than skin and muscle tissues, such as nerves, veins and arteries, needs to be prevented. The system of choice should ideally provide sufficient range of motion such that an optimal fixation location can be chosen which does not compromise the surrounding soft tissues.

Furthermore, during penetration of the soft tissues with a fixation element in order to reach the bony structure, instruments, for instance guiding tubes, may be utilized for guidance of the fixation element while fixating it to the bony structure. Those instruments also serve as a barrier between the fixation element and the soft tissues during application and are known as sleeves or cannulas, protecting these soft tissues including neurovascular tissues from being damaged during fixation of the fixation elements, e.g. bone pins or wires, in or through the bone.

Once a fixation element is connected to a bony structure, a subsequent action comprises the fixation of the fixation element to the system, in particular a connection device, typically in the form of a connection block. In commonly applied embodiments of external fixation systems, the instruments as described for guidance can be separately applied from the other components of a fixation system, such that the instruments are not integrated with that system when in use. In case instruments for guidance during fixation are integrated with the connection system, the risk of procedural errors may be reduced since the order of actions can be dictated by the components of that system. This may result in fewer actions during use of the system, in quicker surgical procedures, and a reduction in therewith associated risks and costs. As such, an system that has integrated instruments for guidance may attribute to an improvement of therapy and care. In addition, a system having integrated instruments may attribute to user-related aspects regarding ease of use, by reducing the total number of actions while using the system, specifically by reducing the number of user-related errors such as repetitive actions and the number of incorrect actions.

The safe use of external fixation systems furthermore relies on correct functioning of the device. Due to the repetitive use of systems, the performance may be compromised. Due to the lack of quality control on critical aspects for correct functioning of reusable connection systems, inferior performance of a system may occur, introducing the risk of system failure. Common failures comprise fatigue and wear of components. Ideally, quality control should test critical aspects of systems after application during a surgical procedure, and affected parts or systems should be replaced in case inferiority is confirmed.

A reusable system which requires quality control and revision after every performed surgical procedure might combine the cost benefits of reusability of a system and the benefits of quality control that disposable systems have. Such a system might comprise of a system that requires multiple subsequent actions during the surgical procedure that established fixation of the system to the bony structures, wherein performing one or more essential actions within this cascade, e.g. the insertion of a locking element for locking a fixation element in a system, can only be performed once, as such that action is an irreversible action. From this approach, the option of reversing the procedure passes. The corresponding risks should be evaluated in the choice of irreversible actions of the surgical procedure. Typically, the subsequent actions required for connecting a connection device to a bony structure with a self-drilling and self-tapping bone pin comprise of:

the making of a surgical incision at the anatomical position of choice;
the spreading of the soft tissues up to the bony structure;
the insertion of a sleeve (guiding tube), in the direction of choice and at the chosen anatomical position;
application of the bone pin to the bone structure through the sleeve (protecting neurovascular and soft tissues from damage during drilling);
removal of the guiding sleeve;
positioning of the connection device;
fixation of the connection device to the bone pin;

The Driving Element and the Locking Element

In a final action of a surgical procedure, the fixation between the connection device and the fixation element is established. The present invention relates to the locking element within the system that receives and locks or holds the fixation element in the system, referred to as the locking action. The locking action establishes the connection between the fixation element and the locking element by radial deformation of the fixation element along its longitudinal axis, such that the outer diameter of the fixation element corresponds to the inner diameter of the deformed locking element. The deformation is established by application of compressive loads that are preferably applied in the longitudinal axis of the fixation element, which equals the longitudinal axis of the locking element, and which is transferred into radial compressive loads.

The radial narrowing of the locking element is preferably caused by elastic deformation of the locking element, such that the geometry of the locking element is not compromised after the locking action is resolved, such that the locking element can be reused. For several reasons, including quality control, it may however be preferred to plastically deform the locking element during the locking action.

In a preferred embodiment, the compressive loads are applied to the locking element via a driving element, applied in the longitudinal axis of the locking element and the fixation element, the driving element enclosing the locking element in the connection element of the connecting device. The geometrical properties of the connection device, the locking element, and the driving element furthermore correspond such that an axial enclosure of the locking element yields to radial compression of the locking element.

In a preferred embodiment, the locking of a fixation element, e.g. a bone pin, in the connection device is established by means of a subassembly consisting of a driving element and a locking element, together also referred to as the locking device. The driving element and the locking element are preferably joined by an enclosing geometry of the driving element for enclosing the geometry of the locking element. The enclosing characteristics may require a temporary, preferably elastic, deformation for establishing the enclosure of the locking element in the driving element, such that the subassembly can be handled as a single part during the procedure known as the surgical procedure.

During the action described as the irreversible action, the driving element may be connected to the locking element using a retaining element. The retaining element may interconnect the locking and the driving element. Previous to this action, the retaining element, the locking element and the driving element may be assembled to a subassembly.

For connecting the assembly as mentioned above, or locking device, to the connection device, a further and preferably separate retaining mechanism is provided. The retaining mechanism retains the locking device, or at least a part thereof, in the connection device. The retaining mechanism may again comprise a separate, second retaining element.

In the action that causes the fixation of the driving element in the locking element, preferably by means of application of a predetermined torsional load that causes compressive loads in the longitudinal axis of the components, deformation of the locking element is established such that the applied load is converted to a compressive load on the bone pin and fixation of the bone pin within in the connection element yields.

The loads that are required for establishing the subassembly (the locking device) consisting of the locking element and the driving element are furthermore lower than the loads required for removing the locking device from the connection device. The retaining mechanism thus requires more force to dissemble than the retaining element between the locking element and the driving element. The retaining mechanism may function by deformation of the locking element. The driving element is thus removed when pulling out the driving element, while the locking element is retained. As such, the irreversible action can be performed without locking the fixation element. In addition, the locking action can be reversed within the surgical procedure while the irreversible action is irreversible during the surgical procedure.

Dissolving the fixation of the bone pin is achieved by loosening the driving element from the locking element, such that the compressive load on the bone pin is reduced and the clamping force between the locking element and the bone pin is dissolved. This property is considered important for adaptation of the relative position of the connection element to the axial direction (longitudinal) of the bone-pin in case of clinically necessity. Under these conditions the locking element is still irreversibly retained in the connection device.

The assembly of the driving element, the locking element, the retaining element, and the bone pin may have the property that the connection between the driving element and the locking element requires less external load for disassembling the subassembly of the driving element and the locking element into separate parts than for the assembly that originates from the irreversible action that encloses the locking element in the connection device. As such, the driving element may be separated from the locking element, while the locking element remains retained in the connection device.

A repetition of the cascade of actions required for fixating the connection device to the bone pin is obstructed by the locking element that is situated within the connection element after the driving element is removed in the process of removing the connection device after a therapy has ended, by obstructing the channel in the connection block that is required for inserting the guiding cannula or sleeve. Removal of the locking element from the connection element allows for performing common actions required for reuse of external device viz. the medical products, including cleaning, quality control, revision, packaging, and sterilization.

In a preferred embodiment, the enclosing geometry of the driving element is established by means of a the retaining element as an additional part assembled to the driving element, allowing for the deformation required for establishing the enclosure of the locking element in the driving element. Such a part may be designed as a ring or slot ring which allows for sufficient elastic deformation such that the ring can be received in a corresponding opening in the driving element, and such that the part holds the locking element retained within the driving element. Also the second retaining element, interconnecting the locking element and the connection device, may have a similar structure, although this part is preferably arranged to exert a higher retaining force than the other retaining element (interconnecting the driving element and the locking element) such the assembly of the locking element and the driving element will disengage, leaving the locking element in the opening connection device.

Although such an embodiment allows for having one or both of the parts as either a disposable or reusable part, it is especially preferred in the specific case that reuse of the system as a whole, including the locking element, is intended, based on the characteristic that the connections between the locking element and the other parts of the system may be reversed without compromising the locking element.

In another preferred embodiment, the functional characteristics of the driving element and the locking element are combined in the same part, said part having the ability of allowing separation of its characteristics into at least one part being a separate driving element and one part being a separate locking device during the action that is described as the irreversible action. The embodiment may consist of multiple parts that are assembled by means of an irreversible method, including the methods of welding, soldering, gluing, screwing, press fitting, and riveting. Such an embodiment is especially preferred in the specific case that the quality control of the system is ensured by having a partially disposable system, the driving element and the locking element being the disposable parts of that system. For such a system, it is furthermore preferred to establish a connection between the connection element and the locking element, such that the system requires a specific action of removal of the disposable locking element from the connection element in order to use the system as a reusable system.

DETAILED DESCRIPTION OF THE FIGURES

In FIGS. 1a-d the steps for connecting a connection device 1 in the form of a connection block to a bone 100 is shown. The connection block 1 is thereto provided with an opening 11 which extends between a first surface 12, which faces the patient 101, and a second surface 13 which faces away from the patient 101. The opening 11 has a section 11a towards the second surface 13 which is provided with threading 14. Towards the patient facing surface 12, the opening 11 is provided with a tapering section 11b wherein the diameter of the opening 11 becomes smaller in the direction of the patient 101, seen along a longitudinal axis A of the opening 11.

Inserted into the opening is a locking device 2 which has a substantially annular shape and is shaped to fit inside the opening 11. The locking device 2 has a flange 21 at one side and deformable tongues 22 at the other side and a body 23 provided there between. The body 23 is provided with threading 24 for cooperation with the threading 14 of the opening. The outer diameter of the body 23 of the locking device 2 thereby corresponds to the diameter of the first section 11a of the opening 11. The length of the body 23 provided with the threading 24 preferably corresponds to the length of the first section 11a of the opening 11, seen along the longitudinal axis A.

The threading 14, 24 fixes the relative position of the locking device 2 and the connection device 1, which position can be adjusted by rotating the locking device 2. In the position as show in FIG. 1a, the lower surface of the flange 21 extends at a distance from the surface 13, such that further movement of the locking device 2 in a direction indicated with I in FIG. 1a is possible, as will be explained in greater detail below. In the situation as shown in FIG. 1a, the tongues 22 of the locking device 2 only partially extend in the tapering section 11b of the opening 11.

Figure 1B:
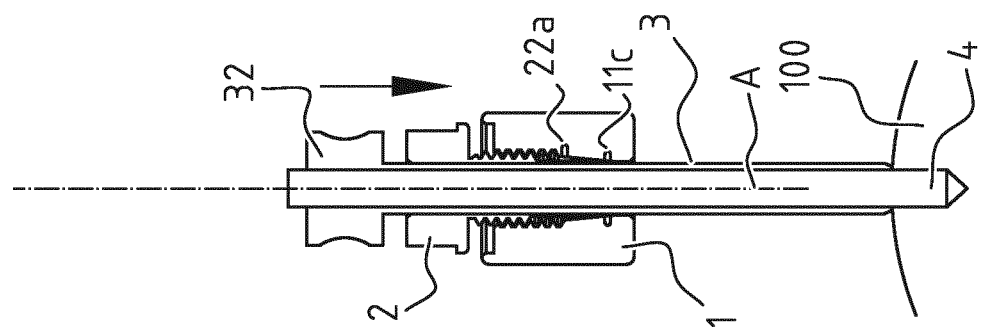

The inner diameter of the locking device 2, including the diameter at the location of the tongues 22, corresponds to the outer diameter d1 of a guiding cannula 3. This limits relative movement of the locking device 2, which also serves as a guiding device for guiding the cannula 3, in a direction along the longitudinal axis A. The guiding cannula 3 is arranged to guide a bone pin 4 from the connection device 1 to the bone 100, see FIG. 1b. In inserted situation as shown in FIG. 1b, the cannula 3 is thereto slidable along the longitudinal axis A with respect to the locking device 2 and thereby with respect to the connection device 2. A flange 32 is provided to allow efficient adjustment of the depth of the cannula 3. This allows efficiently guiding a bone pin 4 to the bone 100, irrespective of the distance between the connection device 1 and the bone 100. When the cannula 3 is advanced sufficiently far such that a distal end 31 abuts the bone 100, the bone pin 4 can be inserted into the cannula 3, schematically indicated with the arrow in FIG. 1b. The inner diameter of the cannula 3 thereto corresponds to the outer diameter of the bone pin 4 such that relative movement of the bone pin 4 in the cannula 3 is again restricted to movement along the longitudinal axis A. The movement of the bone pin 4 with respect to the connection device 1 is therefore also fixed.

Figure 1C:
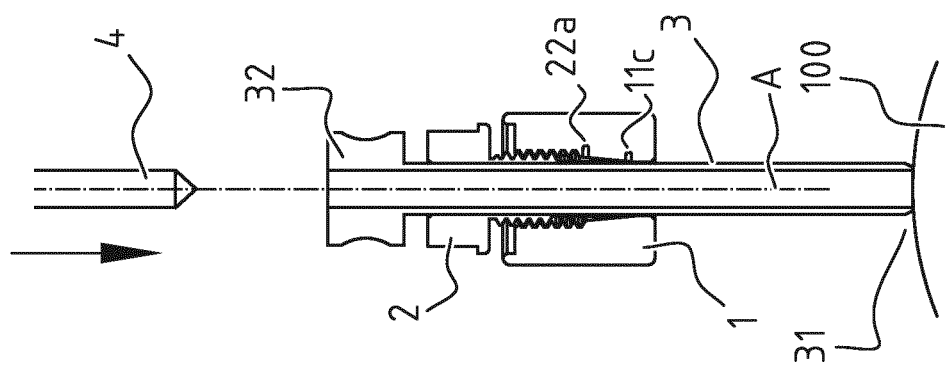

In a next step, see FIG. 1c, the bone pin 4 can be fixed to the bone 100. In this example, self-tapping bone screws 4 are used, such that the bone pins 4 are inserted into the bone 100 by rotating the bone pin 4 inside the cannula 3. The cannula 3 thereby prevents damage to the surrounding tissue of the patient 3. Other bone pins 4 can however be used.

Figure 1D:
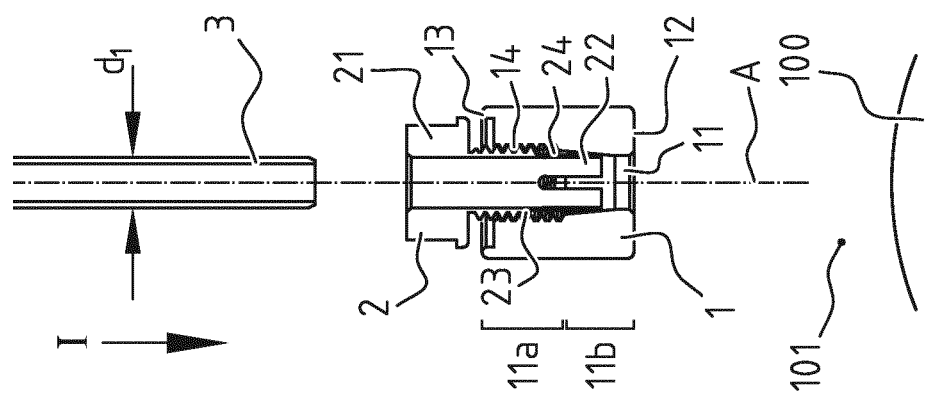

After fixation of the bone pin 4 to the bone 100, the cannula 3 can be withdrawn from the combination of the bone pin 4, the locking device 2 and the connection device 1. This movement is indicated with the arrow in FIG. 1c. As the inner diameter of the locking device 2 corresponds to the outer diameter of the cannula 3, which is larger than the outer diameter of the bone pin 4, the bone pin 4 is held in the locking device 2 with play. Therefore, in order to lock the bone pin 4 with respect to the locking device 2 and thereby with respect to the connection device 1, the locking device 2 is rotated, thereby moving the locking device 2 along the longitudinal axis A, see arrow in FIG. 1d, in the opening 11. The outer surfaces of the tongues 22 will thereby engage the inner surface of the tapering section 11b, urging the tongues 22 radially inwardly, i.e. towards to the longitudinal axis and thereby towards the bone pin 4. The inner surface of the deformable tongues 22 thereby act as engaging surfaces which are arranged to engage the bone pin 4, thereby locking the bone pin 4 with respect to the locking device 2 and thereby the connection device 1. In the locked position as shown in FIG. 1d, the lower surface of the flange 21 of the locking device 2 abuts the upper surface 13 of the connection device 1, which is in this example provided with a correspondingly shaped recess to receive the flange 21 in a countersunk manner.

In this situation, the bone pin 4 is firmly locked with respect to the connection device 1. It will be appreciated, as will be explained in greater detail below, that the bone pin 4 can simply be unlocked by rotating the locking device 2, thereby loosening the tongues 22 such that the locking device 2 is again movable with respect to the bone pin 4.

To however prevent that the locking device 2 is removable from the connection block 1, the system is provided with a retaining mechanism for retaining the locking device 2 in the opening 11 of the connection block 1. The retaining mechanism is exemplary formed by a protrusion 22a on the tongue 22 which engaged in a correspondingly shaped recess 11c in the opening 1. When locking the locking device 2, when moving from FIG. 1c told, the protrusion 22a snaps into the recess 11c. The recess 11c may have a length in longitudinal direction which is longer than the length of the recess to allow some longitudinal movement of the locking device 2 with respect to the connection block 1. The locking device 2 can thus be unlocked, while the retaining mechanism prevents that the locking device 2 can be removed from the connection block by hand.

In the example shown in FIGS. 1a-d, the locking device 2 serves to lock the bone pin 4 and to guide the cannula 3. It is however also possible to use a separate guiding device to guide the cannula 3. Moreover, in the above example, the relative position of the locking device 2 and the connection device 1 is fixed using threading 14, 24. Other means can however be used as will also be shown with reference to FIGS. 2a-d The connection device 1 as shown in FIGS. 2a-d is similar to the connection device 1 as shown in FIGS. 1a-d and is again provided with an opening 11. The diameter of this opening 11 is again larger than the outer diameter d1 of the cannula 3, such that a guiding device 5 is used to limit the relative movement between the cannula 3 and the connection device 1 along the longitudinal axis A, see FIG. 2b. The guiding device 5 again has an annular shape and has an inner diameter corresponding to the outer diameter d1 of the cannula 3. This allows efficient adjustment of the depth of the cannula 3 with respect to the connection device 1 as indicated with double arrow in FIG. 1b. Note that this is different from the locking device 2 as used in FIGS. 1a-d.

Instead of threading, the guiding device 5 is provided with a deformable part 51 which locks into the opening 11 upon inserting the part 51. The deformable part 51 thereby exerts a clamping action of the inner surface of the opening 11, thereby retaining the guiding device 5 in the opening 11 by friction. The guiding device 5 is further provided with a flange 52 for easy manipulation of the guiding device 5.

After insertion of the bone pin 4, see FIG. 2c, the combination of the guiding device 5 and the cannula 3 can be removed from the combination of the bone pin 4 and the connection device 1, see arrow FIG. 2d. As the bone pin 4 is firmly attached to the bone, the combination can be withdrawn by pulling sufficiently hard to overcome the friction of the deformable part 51 of the guiding device 5 or by rotating the guiding device in case of a threaded connection between the guiding device and the connection device. The cannula 3 and the guiding device 5 can hereby be removed in unison.

Although a locking device similar to the locking device as shown in FIGS. 1a-d can be used to lock the bone pin 4 with respect to the connection device 1, for instance by providing corresponding threading, it is also possible to use a locking mechanism formed of two separate parts, as is shown in FIGS. 3a and 3b.

The locking mechanism comprises a driving element 6 and a locking element 7, wherein the annularly shaped locking element 7 is provided with sets of tongues 71, 72 at either side. Both sets of tongues 71, 72 are arranged to move radially inwardly upon deformation, thereby locking the bone pin 4. As an alternative, only one set of tongues may be provided, for instance the upper ones 72. The first set of tongues 71 at the lower side of the locking element 7 are moved radially inwardly upon moving, or driving, the locking element 7 in a direction indicated with the arrow in FIG. 1a. The reduction of the diameter indicated with 19 in the opening 11 will thereby urge the tongues 71 towards the outer surface of the bone pin 4. A groove 11c, similar to the groove in FIGS. 1a-d, is provided near end of the opening 11 towards the patient, wherein ribs 71a of the tongues 71 can snap for locking the relative positions of the locking element 7 with respect to the connection device 1. The ribs 71a form a retaining mechanism for retaining the locking element 7 in the opening 11. In this locked position, the tongues 71 exert a firm clamping action on the bone pin 4 at a location along the longitudinal axis A indicated with the arrow C in FIG. 3b, thereby preventing movement of the bone pin 4.

To further improve the locking action, also or only the tongues 72 provided on the upper side of the locking element 7 will be urged radially inwardly upon movement of the driving element 6 towards the locking element 7. More specifically, the annularly shaped driving element 6 is provided with an opening 61 of which the lower section 64 has a tapering diameter, wherein the diameter increases towards the lower side. The tapering section 64 forms a guiding surface for urging the tongues 72 inwardly, i.e. towards the bone pin 4, when the driving element 6 is moved towards the locking element 7.

Also the tongues 72 can be provided with ribs 72a as second retaining mechanism which can be received in a correspondingly shaped groove 63 at the end of the guiding surface. This connects the driving element 6 to the locking element 7 and thereby to the connecting device 1. In the situation as show in FIG. 3b, the tongues 72 exert a clamping action on the bone pin 4 at a location along the longitudinal axis A indicated with B, at a distance from location C. This improves the locking action of the locking mechanism.

The retaining mechanism C retaining the locking element 7 in the opening 11 of the connection block 1 exerts a larger retaining force than the retaining mechanism B retaining the locking element 7 to the driving element 6. If the driving element 6 is thus removed, for instance by rotating against the threading, the driving element 6 will become lose from the locking element 7 before the locking element 7 becomes loose from the connection block 1. The locking element 7 will thus remain in the opening 11. As the length L1 (corresponding to the height of the connection block 1) is larger than the length L2 of the locking element 7 and the locking element 7 is completely contained in the opening 11, it is difficult, if not impossible, to remove the locking element 7 from the connection block 1 by hand, instead requiring a dedicated tool or toolset for removal. As the inner diameter of the locking element 7 is smaller than the outer diameter of a guide 3 (see FIGS. 2a-d, the system with the retaining locking element 7 can not receive another guide 3, such that the system is not reusable up till removal of the locking element from the connection block.

Instead of ribs 71a, 72a, other movable members may be used to retain the elements together. An example of other movable members in another embodiment is shown in FIGS. 4a-c. The step as shown in FIG. 4a may follow the step as depicted in 2d with similar parts.

In FIGS. 4a-d a connection block 1 similar to the block 1 of FIGS. 2a-d is shown. The opening 11 is at an upper part again provided with threading 14 for interconnecting a driving element 6 which is provided with cooperating threading 64. A lower part of the opening 11 is again provided with a recess 11c in which in this embodiment a ring shaped spring 8 is arranged. The ring shaped spring 8 is a movable member which is movable with respect to the inner surface of the opening 11 and is biased to protrude from said surface.

Figure 6A:
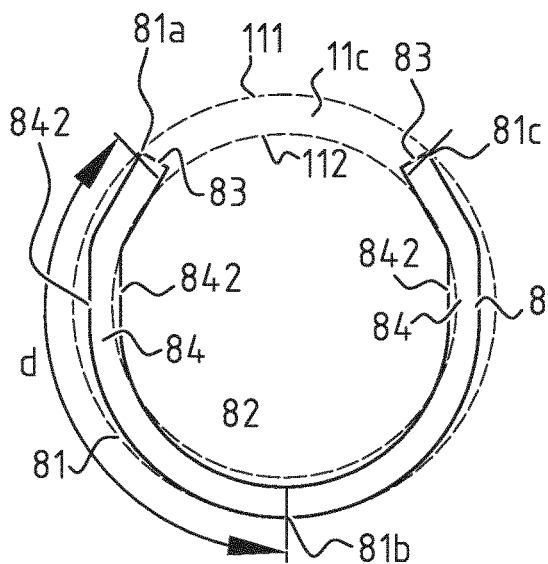
Figure 6B:
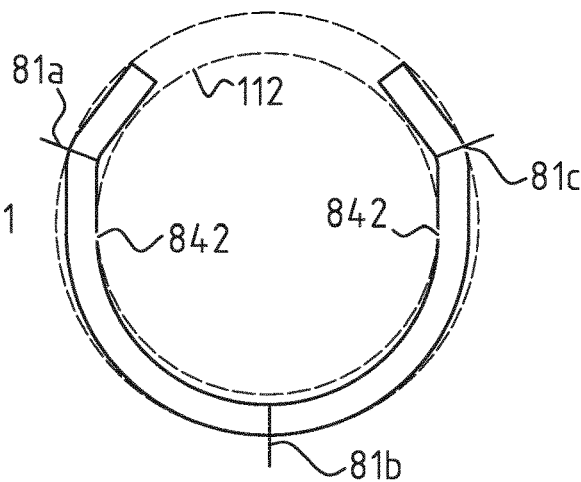
Figure 6C:
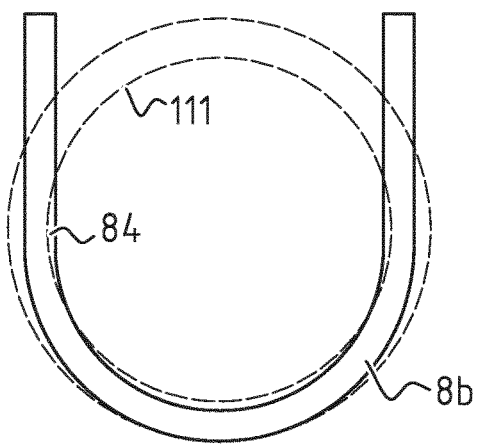
Figure 6D:
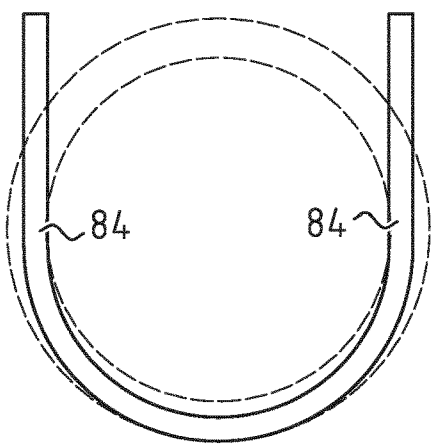
Figure 6E:
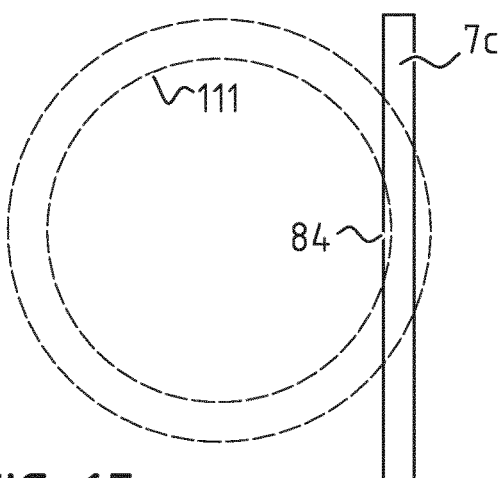
Figure 6F:
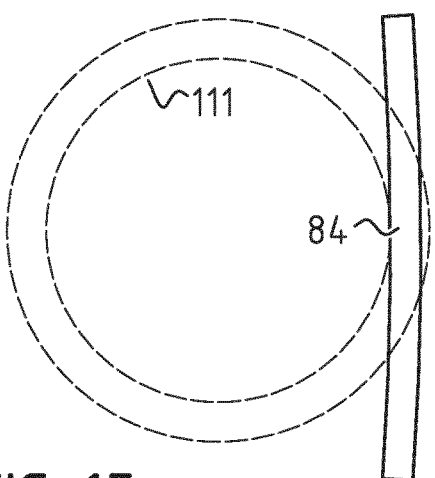

The configuration of the ring shaped spring 8 in the groove 11c according to a preferred embodiment is shown in FIGS. 6a and 6b, which show the cross sections of the groove 11c in the connection block 1 as indicated with the set of arrows in FIG. 4a. FIG. 8 shows a cross-section of the groove 11c in a plane perpendicular to the longitudinal axis A. The contour of the groove 11c is shown in dashed lines and indicates a bottom wall 111 of the groove and an open end 112 (indicated with dashed lines in FIG. 8). The open end 112 is flush with the inner surface 11e of the opening 11. Received in the groove is the ring shaped spring 8 which has the shape of a broken annulus, i.e. an annular sector two thirds of a complete, full annulus. The open part between the ends 83 of the spring 8 provides flexibility to the spring.

The outer and inner surfaces of the spring 8 substantially correspond to the inner diameter and outer diameter of the groove, i.e. of the open end 112 and the bottom 111. The spring 8 is provided with three contact points 81a-c which are provided on a circumscribing circle with the same diameter as the diameter of the bottom wall 111. The three contact points 81a-c are provided at substantially equal mutual distances d (indicated between 81a and 81b in FIG. 6a. This results in a centring of the spring with respect to the opening. When receiving the locking element, two surfaces of the ring shaped spring are in contact therewith.

Substantial rectilinear parts 84 are provided at diametrically opposite locations which protrude from the groove 11c in the blocking position as shown in FIG. 6a. The cross-section of FIG. 8 is taken at these parts 84. The inner surface 842 of the part 84 protrudes from the open end 112. The opposite surface 841 of the part 84 on the other hand lies at a distance from the bottom wall 111 (see the double arrow on the right of FIG. 8). When the spring 8 is urged to the unblocking position as shown in FIG. 6b, the parts 84 will move radially outwardly, accommodated by the space between the surface 841 and the wall 111 until the outer surfaces 842 are flush or even within the open end 112 of the groove 11c. The opening 11 is now unblocked. Due to the spring working of the spring 84, the spring will return to the position as shown in FIG. 6a once the geometry of the locking element 111 allows. In FIGS. 6c-f, two alternative springs 8b, 8c are shown in blocked (6c, 6e) and unblocked (6d, 6f) positions. Also here, parts 84 of the spring can be moved within and without the inner surface (indicated with 111) of the opening 1

Figure 9A:
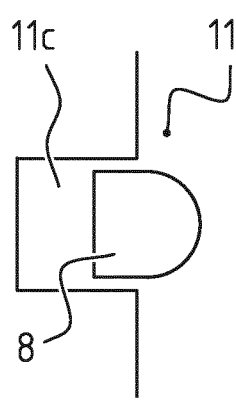
Figures 9B, 9C:
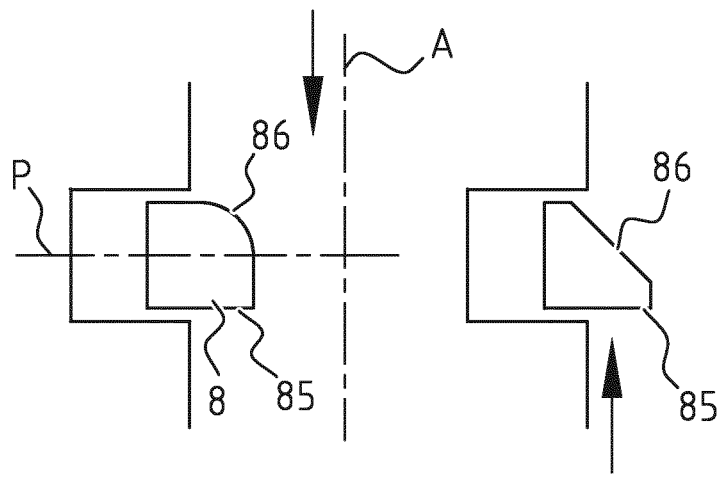
Figure 9D:
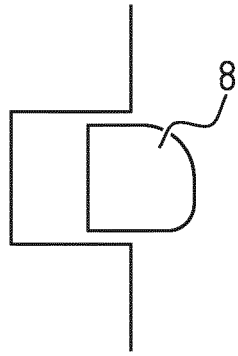
Figure 9E:
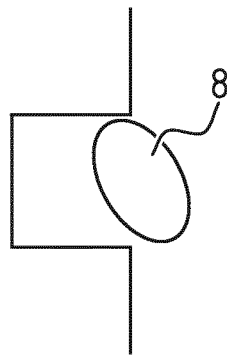
Figure 9F:
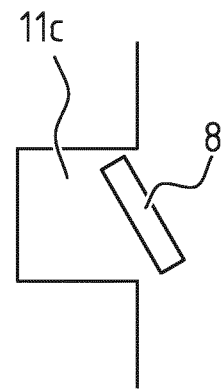

FIGS. 9a-f show different cross-sections of the spring 8, or more generally the movable member. Whereas the cross-section as shown in FIG. 9a has a symmetrical configuration with respect to a plane P (See FIG. 9b) perpendicular to the longitudinal axis A of the opening 11, the cross-sections as shown in FIGS. 9b-9f have an asymmetrical shape with respect to this plane. These configurations have the advantage that a first side (at the top) forms a guiding surface 86 which urges the spring 8 inwardly (to the left in the figures) when an element, such as the locking element, is inserted, which is indicated with the arrow in FIG. 9b. The cross-sections are however barb shaped, such that movement of such an element in the opposite direction, see the arrow in FIG. 9c, will not result in movement to the unblocked position. The lower surfaces 85 preferably are substantially flat (FIGS. 9b-9d) or define an engaging point onto which the element will abut when such an element would be removed from the opening 11.

Back to FIGS. 4a-d, after insertion of the pin 4 in the bone, a combination of the driving element 6 and the locking element 7 is inserted into the opening. The combination has annular shape and has an opening with a diameter corresponding to the diameter of the pin 4. In the opening 61 of the driving element 6 is a groove 61c wherein a ring shaped spring 8b is held, similar to the spring 8 is the opening 11 of the connection block 1. The locking element 7 is provided with groove 71c (see also the cross section of FIG. 5b) wherein the spring 8b is received. A lower part of the locking element 7 is provided with a more longitudinally formed groove (seen along the axis A) for receiving the other spring 8, such that relative motion between the locking element and the connection block for unlocking the bone pin remains possible. The lower part of the locking device 7 has a tapering surface 71e (FIG. 5b).

Upon inserting (indicated with the arrow in FIG. 4a) the combination of the locking element 7 and the driving element 6, which together form a locking device 2 (see for instance FIG. 1) in the framework of the invention, the threading 64 of the driving element 6 will engage the threading 14 in the upper part 11a of the opening 11. Further movement, by rotating the driving element 6, may eventually result in the flange 73 (FIG. 5b) of the locking element 7 abutting the step between the wider upper part 11a and the narrower lower part 11b of the opening 11. Further rotation, thus further insertion of the driving element 6 in the opening 11 will now result in a relative movement between the driving element 6 and the locking element 7. As the driving element 6 and the locking element 7 are provided with cooperating tapered surfaces 72 64, this movement will result in the tongues 72 moving inwardly, see the front view of FIG. 5a. Generally speaking, relative movement of the driving part 6 with respect to the locking device 7 will lock the bone pin 4 in the locking element.

Upon further inserting the combination of the locking element 7 and the driving element 6, the tapered surfaces 71e will upon contacting the spring 8, which protrudes from the surface of the wall of the opening 111 (FIG. 6a), urge the spring backwardly (FIG. 6b). Further movement will result in the spring locking into the groove 71d, the spring restoring its shape to the initial shape (FIG. 6a). The locking element 7 is now locked in the connection block 1.

With reference to FIG. 4b, the system comprises two retaining mechanisms, the location of which are generally indicated with arrows B and C. The retaining force of the first retaining mechanism C, thus the friction between the connection block 1 and the locking element 7, is larger than the retaining force of the second retaining system B, the friction between the locking element 7 and the driving element 6. If the driving element 6 would thus be removed, it will separate from the locking element 7 before the locking element 7 will separate form the connection block 1. The locking element 7 is thus retaining in the connection element 1, thereby blocking the opening 11 for further insertion of a guiding tube 3. Upon removal of the driving element 7, the tongues 72 will move outwardly (FIG. 4c), which allows removal of the bone pin 4 (FIG. 4d). The locking element 7 is hereby completely contained in the opening.

In the above example, similar ring shaped spring elements 8, 8b are used. In order to obtain a larger friction force in the first retaining mechanism C, the diameter of the spring element 8 if larger than the diameter of the spring element 8b, thereby resulting in a higher spring constant. Differences in stiffness may however also result from differences in e.g. cross sectional geometry or material properties.

The connection system is particularly suitable to connect a connection device to a bone or bone fragment with two parallel bone pins. Such a system is in FIG. 7, using two connection block 1a, 1b with a correcting system 130 in between. Although in this figure a connection system is shown which corresponds to the system as shown in FIGS. 1a-d, it will be appreciated that the same applies to the system as shown in FIGS. 2-6, or combinations thereof.

The present invention is not limited to the embodiment shown, but extends also to other embodiments falling within the scope of the appended claims.

The invention claimed is:

1. A system for connecting a connection device to a bone with a bone pin, wherein the system comprises a connection device provided with an opening for receiving the bone pin, and wherein the system further comprises a locking device arranged to be received in the opening of the connection device and which is arranged to engage the bone pin for locking the bone pin with respect to the connection device, wherein the locking device is movable between a locked position,
wherein the bone pin is locked with respect to the connection device, and an unlocked position wherein the bone pin is movable with respect to the connection device, characterized in that the system further comprises a blocking mechanism comprising a retaining mechanism arranged for retaining said locking device in the opening for preventing removal by hand of said locking device from said opening for at least partially blocking the opening in the connection device after removal of the bone pin from the opening.

2. The system according to claim 1, wherein the blocking mechanism comprises a movable member which is movable to a position within the opening for blocking said opening, wherein the locking device is provided with the movable member.

3. The system according to claim 2, wherein the movable member is arranged to interlock the locking device and the connection device.

4. The system according to claim 3, wherein the connection device is provided with a recess for receiving said movable member for retaining the locking device in the opening.

5. The system according to claim 4, wherein the movable member is formed as a ring-shaped member received in a groove formed in an opening of the locking device, wherein the ring-shaped member is movable between a blocking position wherein the ring-shaped member protrudes from said groove and an unblocked position wherein the ring-shaped member does not protrude from said groove.

6. The system according to claim 5, wherein in the blocked position at least a part of the ring-shaped member lies at a distance from the bottom of the groove.

7. The system according to claim 5, wherein the part of the ring-shaped member which protrudes from said groove lies at a distance from the bottom of the groove.

8. The system according to claim 5, wherein the ring-shaped member comprises at least two diametrically opposed parts protruding from the groove.

9. The system according to claim 5, wherein the surface adjacent to the bottom of the groove comprises at least three contact points at mutual distances on a circle having a diameter corresponding to the diameter of the bottom surface of said groove for aligning said ring-shaped member in the opening of the connection device.

10. The system according to claim 2, wherein the movable member is formed as a barb to facilitate passing of the locking device in a first direction when the locking device is inserted, whereas passing in the opposite direction is prevented.

11. The system according to claim 1, wherein the retaining mechanism is arranged for preventing removal of said locking device from said opening when the locking device is moved from the locked to the unlocked position.

12. The system according to claim 11, wherein the connection device and the locking device are provided with cooperating interconnecting means,
wherein the retaining mechanism is arranged to operate separately from the interconnecting means.

13. The system according to claim 1, further comprising a guiding tube arranged to guide the bone pin from the connection device to the bone for connecting the bone pin to the bone, wherein the inner diameter of the guiding tube corresponds to the outer diameter of the bone pin and wherein the guiding tube can be slidably received in the opening, the guiding tube being slidable with respect to the connection device along an axis parallel to the longitudinal axis of the opening.

14. The system according to claim 13, wherein the outer diameter of the guiding tube is larger than the inner diameter of the locking device.

15. The system according to claim 13, wherein the guiding tube is movable with respect to the connection device and bone pin such that the guiding tube is removable from the combination of the bone pin and the connection device and wherein the locking device is arranged to lock the bone pin after removal of the guiding tube.

16. The system according to claim 1, wherein the connection device and/or the locking device is made from a metal or a plastic.

17. A system for connecting a connection device to a bone with a bone pin, wherein the system comprises a connection device provided with an opening for receiving the bone pin, and wherein the system further comprises a locking device arranged to be received in the opening of the connection device and which is arranged to engage the bone pin for locking the bone pin with respect to the connection device,
wherein the locking device is movable between a locked position, wherein the bone pin is locked with respect to the connection device, and an unlocked position wherein the bone pin is movable with respect to the connection device, wherein the locking device comprises an engaging surface for engaging the bone pin, wherein the engaging surface is movable towards and from said bone pin between an unlocked position, wherein the bone pin is movable with respect to the engaging surface, and a locking position, wherein the engaging surface engages the bone pin for locking said bone pin with respect to the connection device by clamping, wherein the locking device comprises an engaging element provided with at least one engaging surface for engaging the bone pin for locking said pin and a separate driving element arranged to move the engaging element along the longitudinal axis of the opening for moving the engaging surface from the unlocked to the locked position, characterized in that the system further comprises a blocking mechanism comprising a retaining mechanism arranged for retaining said locking device in the opening for preventing removal by hand of said locking device from said opening for at least partially blocking the opening in the connection device after removal of the bone pin from the opening, wherein the retaining mechanism is a first retaining mechanism arranged to retain the engaging element of the locking device in the opening after removal of the driving element, wherein the system further comprises a second retaining mechanism for retaining the engaging element and the driving element, and wherein the retention force of the first retaining mechanism between the engaging element and the connection device is larger than the retention force of the second retaining mechanism between the engaging element and the driving element.

18. System according to claim 17, wherein the engaging element is completely retained in the opening.

19. The system according to claim 17, wherein both retaining mechanisms are provided with a ring-shaped member, wherein the spring constants of said ring-shaped members are different.

20. The system according to claim 19, wherein the diameter of the ring-shaped element of the second retaining mechanism is larger than the diameter of the retaining mechanism between the engaging element and the driving element.

21. The system according to claim 17, wherein the driving element and the connection device are provided with cooperating connecting means.

* * * * *